United States Patent
Guo et al.

(10) Patent No.: US 10,133,964 B2
(45) Date of Patent: Nov. 20, 2018

(54) MAGNETIC RESONANCE IMAGE RECONSTRUCTION SYSTEM AND METHOD

(71) Applicant: Siemens Healthcare GmbH, Erlangen (DE)

(72) Inventors: Yi Guo, Los Angeles, CA (US); Boris Mailhe, Plainsboro, NJ (US); Xiao Chen, Somerset, NJ (US); Mariappan S. Nadar, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 122 days.

(21) Appl. No.: 15/471,079

(22) Filed: Mar. 28, 2017

(65) Prior Publication Data
US 2018/0285695 A1 Oct. 4, 2018

(51) Int. Cl.
*G06K 9/66* (2006.01)
*G06T 11/00* (2006.01)
(Continued)

(52) U.S. Cl.
CPC ............... *G06K 9/66* (2013.01); *A61B 5/055* (2013.01); *A61B 5/7267* (2013.01);
(Continued)

(58) Field of Classification Search
CPC .... G06K 9/66; G06K 9/0014; G06K 9/00147; G06K 9/4628; G06K 9/6267;
(Continued)

(56) References Cited

U.S. PATENT DOCUMENTS

| 5,526,446 A | 6/1996 | Adelson et al. |
| 6,243,489 B1 | 6/2001 | Delong |

(Continued)

FOREIGN PATENT DOCUMENTS

WO    WO 2017113205 A1 *  7/2017 ............. A61B 5/055

OTHER PUBLICATIONS

"V-Net: Fully Convolutional Neural Networks for Volumetric Medical Image Segmentation"; Milletari, Fausto; 2016 Fourth International Conference on 3D Vision (3DV); Dec. 19, 2016.*

(Continued)

*Primary Examiner* — Michael Osinski

(57) ABSTRACT

A method for training a system for reconstructing a magnetic resonance image includes: under-sampling image data from each of a plurality of fully-sampled images; and inputting the under-sampled image data to a multi-scale neural network comprising sequentially connected layers. Each layer has an input for receiving input image data and an output for outputting reconstructed image data. Each layer performs a process comprising: decomposing the array of input image data; applying a thresholding function to the decomposed image data, to form a shrunk data, the thresholding function outputting a value asymptotically approaching one when the thresholding function receives an input having a magnitude greater than a first value, reconstructing the shrunk data for combining with a reconstructed image data output by another one of the layers to form updated reconstructed image data, and machine-learning at least one parameter of the decomposing, the thresholding function, or the reconstructing.

20 Claims, 10 Drawing Sheets

(51) Int. Cl.
*G06T 7/00* (2017.01)
*A61B 5/055* (2006.01)
*A61B 5/00* (2006.01)

(52) U.S. Cl.
CPC .......... *G06T 7/0012* (2013.01); *G06T 11/008* (2013.01); *G06T 2207/10088* (2013.01)

(58) Field of Classification Search
CPC ................ G06T 11/008; G06T 7/0012; G06T 2207/10088; G06T 2207/10024; G06T 2207/30004; A61B 5/055; A61B 5/7267; G06N 3/04; G06N 3/08; G06N 3/0454; G06N 3/084
See application file for complete search history.

(56) References Cited

U.S. PATENT DOCUMENTS

| | | | | |
|---|---|---|---|---|
| 9,097,780 | B2* | 8/2015 | Liu | G01R 33/5611 |
| 9,563,825 | B2* | 2/2017 | Shen | G06K 9/66 |
| 9,918,639 | B2* | 3/2018 | Cetingul | A61B 5/7289 |
| 10,012,717 | B2* | 7/2018 | Wang | G01R 33/5611 |
| 10,061,972 | B2* | 8/2018 | Champlin | G06K 9/0014 |
| 2016/0140408 | A1* | 5/2016 | Shen | G06K 9/4676 |
| | | | | 382/157 |
| 2016/0148078 | A1* | 5/2016 | Shen | G06K 9/66 |
| | | | | 382/158 |
| 2016/0174902 | A1 | 6/2016 | Georgescu et al. | |
| 2016/0328643 | A1 | 11/2016 | Liu et al. | |
| 2017/0140236 | A1* | 5/2017 | Price | G06K 9/4628 |
| 2017/0160363 | A1* | 6/2017 | Chen | G01R 33/5608 |
| 2017/0161545 | A1* | 6/2017 | Champlin | G06K 9/0014 |
| 2017/0200092 | A1* | 7/2017 | Kisilev | G06N 99/005 |
| 2017/0301095 | A1* | 10/2017 | Zhang | G06T 7/12 |
| 2018/0253839 | A1* | 9/2018 | Zur | A61B 1/00009 |
| 2018/0268256 | A1* | 9/2018 | Di Febbo | G06K 9/6256 |
| 2018/0268526 | A1* | 9/2018 | Mentl | G06N 3/08 |

OTHER PUBLICATIONS

Yuan, Ming, "Nonnegative Garrote Component Selection in Functional ANOVA Models", Proceedings of the Eleventh International Conference on Artificial Intelligence and Statistics (AISTATS-07), Mar. 21-24, 2007, San Juan, Puerto Rico, pp. 660-666.

Hammernik, Kerstin, et al. "Learning a Variational Model for Compressed Sensing MRI Reconstruction", ISMRM 24th Annual Meeting & Exhibition, May 7-13, 2016, Singapore, 7pgs.

Selesnick, Ivan, "Penalty and Shrinkage Functions for Sparse Signal Processing", Connexions, Nov. 16, 2012 (http://cnx.org/content/m45134/1.1/) 26 pgs.

* cited by examiner

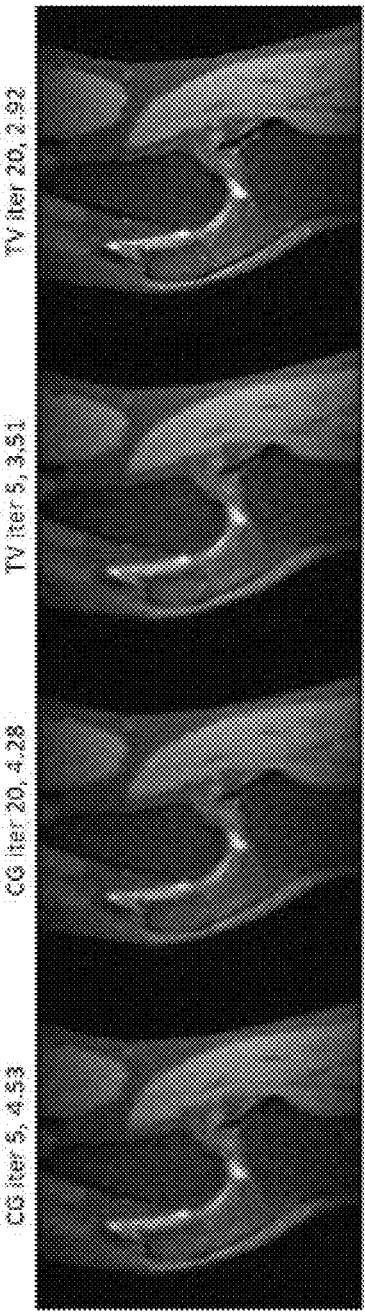

MAGNETIC RESONANCE IMAGE RECONSTRUCTION SYSTEM AND METHOD

FIELD

This disclosure relates to magnetic resonance (MR) imaging generally, and more specifically to MR image reconstruction.

BACKGROUND

Magnetic Resonance Imaging (MRI) is a powerful biomedical tool to non-invasively image the human body for disease diagnosis and healthy physiological process research. MRI is intrinsically slow, and numerous methods have been proposed to accelerate the MRI scan. One of the most important acceleration method is the under-sampling reconstruction technique, where fewer samples are acquired in the MRI data space (k-space), and prior knowledge is used to restore the images. The MRI image reconstruction problem is often formulated as an optimization problem with constraints, and iterative algorithms, such as non-linear conjugate gradient (NLCG), fast iterated shrinkage/thresholding algorithm (FISTA), alternating direction method of multipliers (ADMM), Broyden-Fletcher-Goldfarb-Shanno (BFGS) quasi-Newton method, or the like. are used to solve the optimization problem.

SUMMARY

In some embodiments, a method for training a system for reconstructing a magnetic resonance (MR) image from signals collected by an MR scanner comprises: under-sampling respective image data from each of a plurality of fully-sampled images; inputting the under-sampled image data to a multi-scale neural network comprising a plurality of sequentially connected layers, each layer having a respective input for receiving a respective array of input image data and an output for outputting reconstructed image data, each layer performing a recursive process comprising: decomposing the array of input image data received at the input of the layer; applying a thresholding function to the decomposed image data, to form a shrunk data, the thresholding function outputting a non-zero value asymptotically approaching one in the case where the thresholding function receives an input having a magnitude greater than a first value, reconstructing the shrunk data for combining with a reconstructed image data output by another one of the plurality of layers to form updated reconstructed image data, and machine-learning at least one parameter of the decomposing, the thresholding function, or the reconstructing based on the fully sampled images and the updated reconstructed image data.

In some embodiments, a system for acquiring and reconstructing a magnetic resonance (MR) image from signals collected by an MR scanner comprises: a non-transitory machine readable storage medium for storing under-sampled image data from a plurality of fully-sampled images; a multi-scale neural network for receiving the under-sampled image data, the multi-scale neural network comprising a plurality of sequentially connected layers, each layer having a respective input for receiving a respective array of input image data and outputting reconstructed image data, each layer configured for performing a process comprising: decomposing the array of input image data received at the input of the layer, applying a thresholding function to the decomposed image data, to form a shrunk data, the thresholding function outputting a non-zero value asymptotically approaching one in the case where the thresholding function receives an input having a magnitude greater than a first value, reconstructing the shrunk data for combining with a reconstructed image data output by another one of the plurality of layers to form updated reconstructed image data, and machine-learning at least one parameter of the decomposing, the thresholding function, or the reconstructing based on the fully sampled images and the updated reconstructed image data; and an MR scanner for acquiring additional under-sampled image data from a subject for reconstruction using the multi-scale neural network and the at least one parameter.

In some embodiments, a non-transitory, machine readable storage medium is encoded with computer program software, such that when a processor executes the computer program software, the processor performs a method for training a system for reconstructing a magnetic resonance (MR) image from signals collected by an MR scanner. The method comprises: under-sampling respective image data from each of a plurality of fully-sampled images; inputting the under-sampled image data to a multi-scale neural network comprising a plurality of sequentially connected layers, each layer having a respective input for receiving a respective array of input image data and an output for outputting reconstructed image data, each layer performing a recursive process comprising: decomposing the array of input image data received at the input of the layer; applying a thresholding function to the decomposed image data, to form a shrunk data, the thresholding function outputting a non-zero value asymptotically approaching one in the case where the thresholding function receives an input having a magnitude greater than a first value, reconstructing the shrunk data for combining with a reconstructed image data output by another one of the plurality of layers to form updated reconstructed image data, and machine-learning at least one parameter of the decomposing, the thresholding function, or the reconstructing based on the fully sampled images and the updated reconstructed image data.

BRIEF DESCRIPTION OF THE DRAWINGS

FIG. 8A shows a fully sampled MRI image.

FIGS. 8B, and 8E, 8F, 8G, and 8H show under-sampled images reconstructed by a variety of methods.

FIGS. 8C and 8D show under-sampled images reconstructed using the system of FIGS. 1-3B, before and after training, respectively.

DETAILED DESCRIPTION

Figure 1:
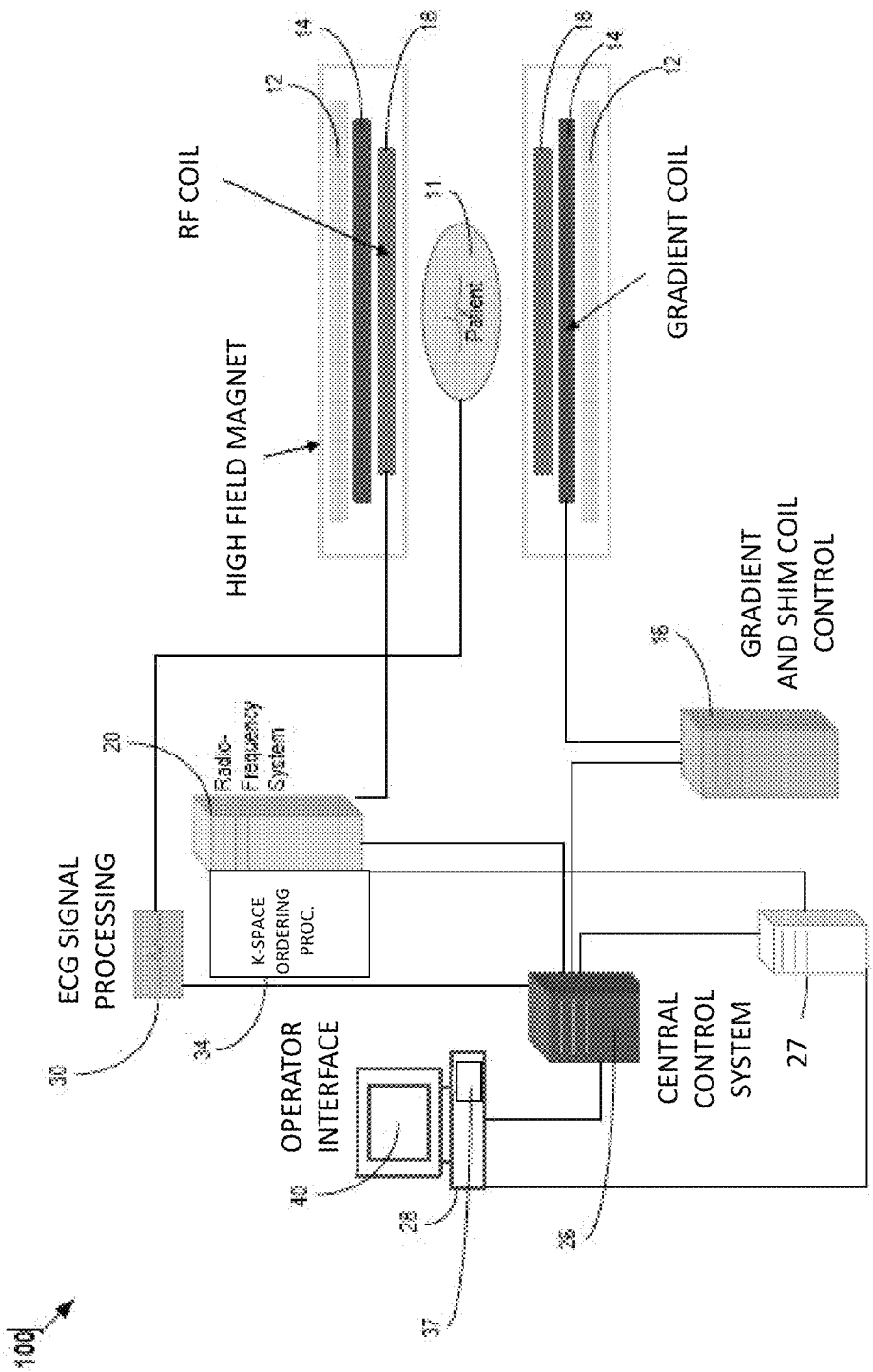
FIG. 1 is a block diagram of an embodiment of an MR system for medical imaging.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

Various iterative MR image reconstruction algorithms provide respectively different performance. Iterative methods involve performing a large number of iterations before the results converge, and the regularization parameters are tuned to get optimal performance. The tuning can be expressed as a minimization problem. Given a set of raw MR data, the image reconstruction is performed several times using different parameter values, and the set of values resulting in the minimum error are selected. This minimization can be expressed as:

$$x = \underset{x}{\mathrm{argmin}} \|Ax - y\|_2^2 + \lambda \|Tx\|_1 \quad (1)$$

where x is the target image to be reconstructed, and y is the under-sampled raw k-space data. A is the MRI model to connect the image to MRI-space (k-space), which can involve a combination of an under-sampling matrix U, a Fourier transform F, and sensitivity maps S. T represents a sparsifying (shrinkage) transform. λ is a regularization parameter. The l1 norm is used to enforce sparsity in the transform domain. $\|Ax-y\|_2^2$ is the l2 norm of the variation of the under-sampled k-space data. Generally, the lp norm is $$\sqrt[p]{\sum |x|^p}.$$

In some embodiments, the operator T is a wavelet transform. In other embodiments, the operator T is a finite difference operator in the case of Total Variation regularization.

Numerous iterative algorithms can be used to solve this kind of optimization problem, but in general, they have the following recursive update step for each iteration:

$$x_{t+1} = x_t + \alpha A^H(Ax_t - y) + T^H \mathrm{shrink}(Tx_t) \quad (2)$$

where α is the gradient step size that is to be determined by manual tuning, and shrink is a threshold operation to solve the l1 norm given by $\|x\|_1 = \Sigma_t |x_t|$. In manual tuning methods, the parameters are hand-tuned, and their selection is not part of the image reconstruction algorithm. Image reconstruction is the task of obtaining the image from measurements at each scan. Often such an iterative method involves 40-200 iterations of the reconstruction to find the optimum (e.g., minimum squared error) image corresponding to that scan.

This disclosure describes examples based on machine learning. The processing is split into two phases: an offline training phase where the goal is to identify an optimal set of reconstruction parameters that can be applied to many different images, and an online processing phase in which new MR data are scanned and the goal is to reconstruct the images using the reconstruction parameters learned during the training phase.

This disclosure describes a system and method using a deep neural network (DNN) for magnetic resonance (MR) image reconstruction. In some embodiments, data are input to the DNN to learn directly from the data what T should be and what λ should be in equation (2) for a given under-sampling operator S (i.e., for a given MRI model A). Once the trained system is deployed with the set of decomposition, thresholding and reconstruction parameters learned during training, the system can reconstruct new images very quickly from new MR data that under-sampled using the same sampling mask used during training. For example, results achieved with the trained five-stage or six-stage DNN system according to this disclosure are comparable to results achieved by a general manually tuned system having 40-200 iterations.

Each layer of the network corresponds to a respective iteration of the MRI reconstruction model. An image of any size can be divided into a plurality of patches having a predetermined size (e.g., 5×5, 7×7, 9×9, 11×11 or the like). Each patch is subjected to multi-scale decomposition, thresholding and reconstruction. During training, a set of known full-scale images are under-sampled with a given sampling operator (mask) and processed. Based on the known full-scale images and the reconstructed images, the decomposition, thresholding and/or reconstruction parameters are obtained by a machine-learning algorithm such as backpropagation, RMSprop or ADAM. These machine-learned computed parameters can subsequently be used during clinical operation to rapidly reconstruct images. The system combines the advantages of patch-based representations with the computational efficiency of multiscale transforms.

System Architecture

FIG. 1 shows a system 100 for ordering acquisition of frequency domain components representing Magnetic Resonance (MR) image data for storage in a k-space storage array, as used by some embodiments. In system 100, magnetic coils 12 create a static base magnetic field in the body of patient 11 to be positioned on a table and imaged. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MR imaging device magnetic field resulting from patient anatomical variation and other sources. The magnetic field gradients include a slice-selection gradient magnetic field, a phase-encoding gradient magnetic field and a readout gradient magnetic field that are applied to patient 11.

Further RF (radio frequency) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives MR signals, i.e., signals from the excited protons within the body as they return to an equilibrium position established by the static and gradient magnetic fields. The MR signals are detected and processed by a detector within RF module 20 and k-space component processor unit 34 to provide an MR dataset to an image data processor for processing into an image. In some embodiments, the image data processor is located in central control unit 26. However, in other embodiments such as the one depicted in FIG. 1, the image data processor is located in a separate unit 27. ECG synchronization signal generator 30 provides ECG signals used for pulse sequence and imaging synchronization. A two or three dimensional k-space storage array of individual data elements in k-space component processor unit 34 stores corresponding individual frequency components comprising an MR dataset. The k-space array of individual data elements has a designated center and individual data elements individually have a radius to the designated center.

A magnetic field generator (comprising coils 12, 14 and 18) generates a magnetic field for use in acquiring multiple individual frequency components corresponding to individual data elements in the storage array. The individual frequency components are successively acquired using a Cartesian acquisition strategy as the multiple individual frequency components are sequentially acquired during acquisition of an MR dataset representing an MR image. A storage processor in the k-space component processor unit 34 stores individual frequency components acquired using the magnetic field in corresponding individual data elements in the array. The row and/or column of corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components is substantially minimized.

Central control processor 26 is programmed to sample the MR signals according to a predetermined sampling pattern. Central control unit 26 also uses information stored in an internal database to process the detected MR signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Display processor 37 processes the magnetic resonance signals to provide image representative data for display on display 40, for example.

MR scanning system 100 is only exemplary, and a variety of MR scanning systems can be used to collect the MR data.

Figure 2:
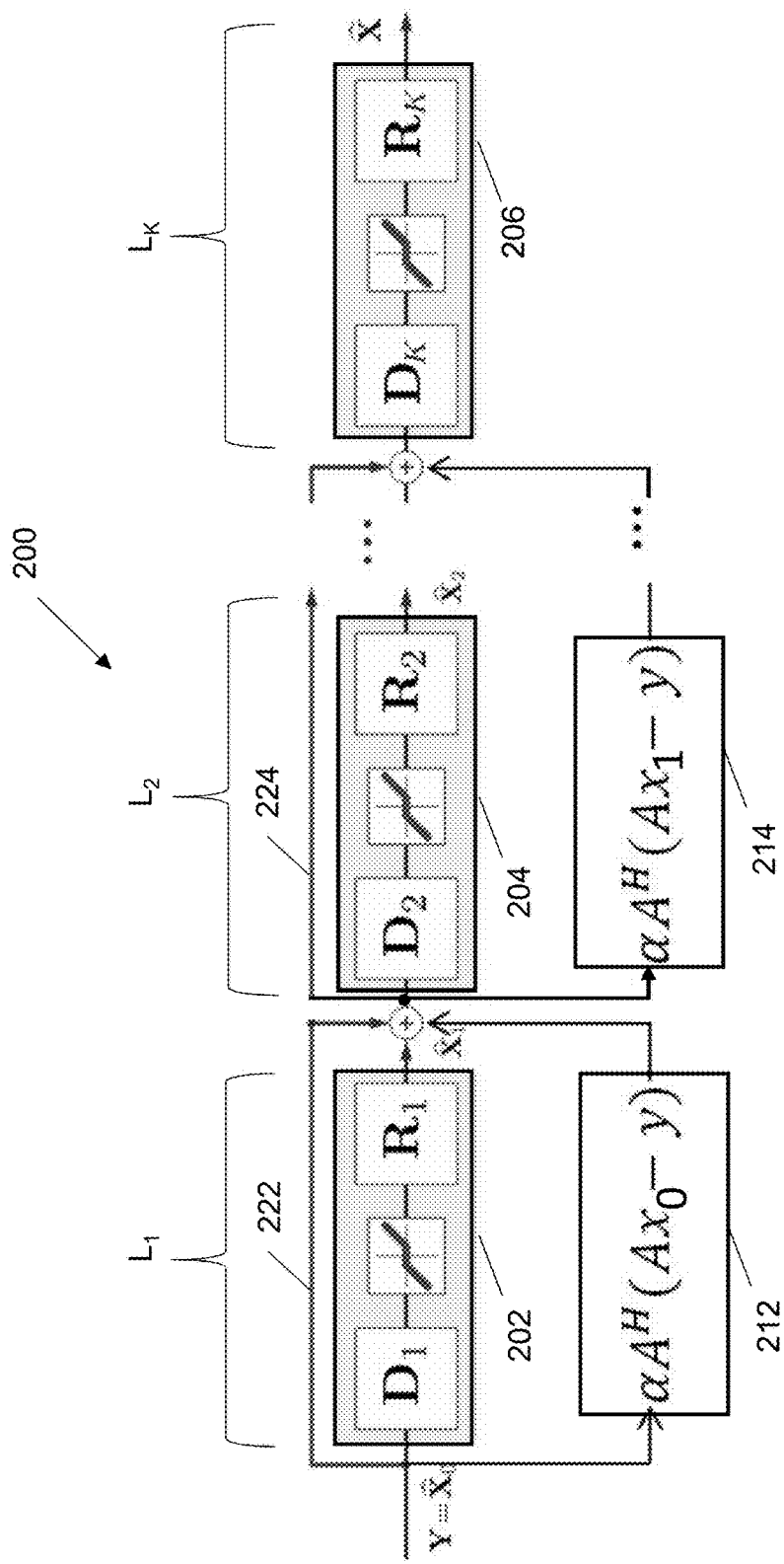
FIG. 2 is a block diagram of a deep neural network for MR image reconstruction according to some embodiments.

FIG. 2 is an illustration of a deep unfolding system 200 for reconstructing MR images, as it can be applied in some embodiments. The layers $L_1, L_2, \ldots, L_K$ shown in FIG. 2 form a neural network with K layers corresponding to specific operations of a recursive algorithm. Block 202, 204 and 206 contain respective $D_i$ and $R_i$ linear operations. The $D_i$ and $R_i$ operators each include a respective bank of filters, discussed in the description of FIG. 3B. In FIG. 2, the $D_i$ operator functions as an edge detector. The threshold operator $S_i$ performs a shrinkage function by zeroing out the weakest convolved coefficients output from the filters of the D operator, but does not change the size of the data array. The blocks 202, 204 and 206 are convolution/deconvolution and threshold layer that represents the l1 norm minimization, i.e., the $T^H$shrink $(Tx_t)$ component of equation (2). The blocks 212 and 214 represent the gradient update component $\alpha A^H(Ax_t-y)$ of equation (2) with step size $\alpha$. In each layer $L_1, L_2, \ldots, L_K$, the input image data, the reconstructed output data from the $R_i$ operator and the gradient step size update are provided to a respective summation node, where they are added together to update and further refine the image data.

In some embodiments, the step size $\alpha$, the convolution filter weights and threshold value, and other model parameters are learned from a training data set. A series of fully-sampled images are used to train the network.

Depending on the system and training images used, the number of training images and the number of times the data are fed into the training algorithm can vary. In some embodiments, a signal-to-noise ratio (SNR) is computed after training with a set of under-sampled images to see whether the SNR is at least a threshold value (e.g., 20). In other embodiments, mean squared error (MSE) data are computed after training with a set of under-sampled image data to see whether the MSE is below a threshold value. In either case, if the SNR or MSE criterion is not met, an additional set of under-sampled training images are reconstructed beginning with the learned parameters from the previous training. The learned parameters are refined further, and the sequence is repeated until the SNR or MSE criterion is passed.

The system 200 performs MRI reconstruction with speed and accuracy without manual tuning. That is, for a given under-sampling operator, the step size $\alpha$, the convolution filter weights and thresholding function parameter are computed based on a fully sampled set of known images and a corresponding set of images reconstructed from an under-sampled set of data from the fully sampled set of known images. In some embodiments, as few as five iterations (i.e., layers) are sufficient to reach good images quality. The parameters of the reconstruction, including the constraint weights (realized by convolution layers), are learned from the data, and are subsequently able to achieve better results on new images in very small number of iterations.

The D operator has a bank of filters, and performs decomposition by convolving each individual filter with the image data. The D operator computes the result of applying each individual filter to the input image, and outputs a plurality of filter response arrays, each representing a transform of the image data by a respectively different filter. Each of the filter response arrays contains a plurality of coefficients. For example, one of the filters can be a 5×5 or 7×7 array of coefficients. The thresholding operator has a thresholding nonlinearity that zeroes out any coefficients having values less than a threshold value, and outputs shrunk data. The R operator is a reconstruction operator implemented with deconvolution. The filter of the R operator is applied to the shrunk data to return the shrunk data to the image domain, and the output values of the R operator are added together to provide a total reconstructed image data. The output of the R operator is a single array having the size of the image.

The D and R operators efficiently operate on images of arbitrary sizes. In some embodiments, the network is trained by adjusting the weights (coefficients) in the layers $D_i$ and $R_i$ to minimize a specific loss function between the "ground truth" (i.e., fully sampled, clean training) images and their corresponding reconstructed under-sampled images. In some embodiments, the network is trained by adjusting parameters controlling the shape of the thresholding function. In some embodiments, the network is trained by adjusting the weights (coefficients) in the layers $D_i$ and $R_i$ and parameters controlling the shape of the thresholding function. The loss functions applied by the system 200 can be a minimization of mean squared error (MSE) or a maximization of structural similarity (SSIM), for example. In some embodiments, after training, the network provides efficient operators for fast MR image reconstruction, using the coefficients and parameters computed during training.

The system 200 illustrated in FIG. 2 provides automatic tuning (i.e., automatic computation of the D filter coefficients, the thresholding operator parameter, and the R filter coefficients). There is no need for manual tuning of the regularization parameters.

For reconstruction of images in a clinical setting (using a previously trained system), the reconstruction time can be controlled by varying the depth of the network. For training purposes, the D filter coefficients, the thresholding operator parameter, and the R filter coefficients can be ascertained from a network having five or six layers.

To achieve these benefits, over-complete patch dictionaries are used herein as domains for sparse image representation. That is, each p×q patch is decomposed as a linear combination of the atoms in a dictionary D, a threshold is applied to the computed coefficients, and then the sparsified image is reconstructed with an inverse transformation R. The resulting image is then assembled by averaging overlapping patches.

Figure 3:
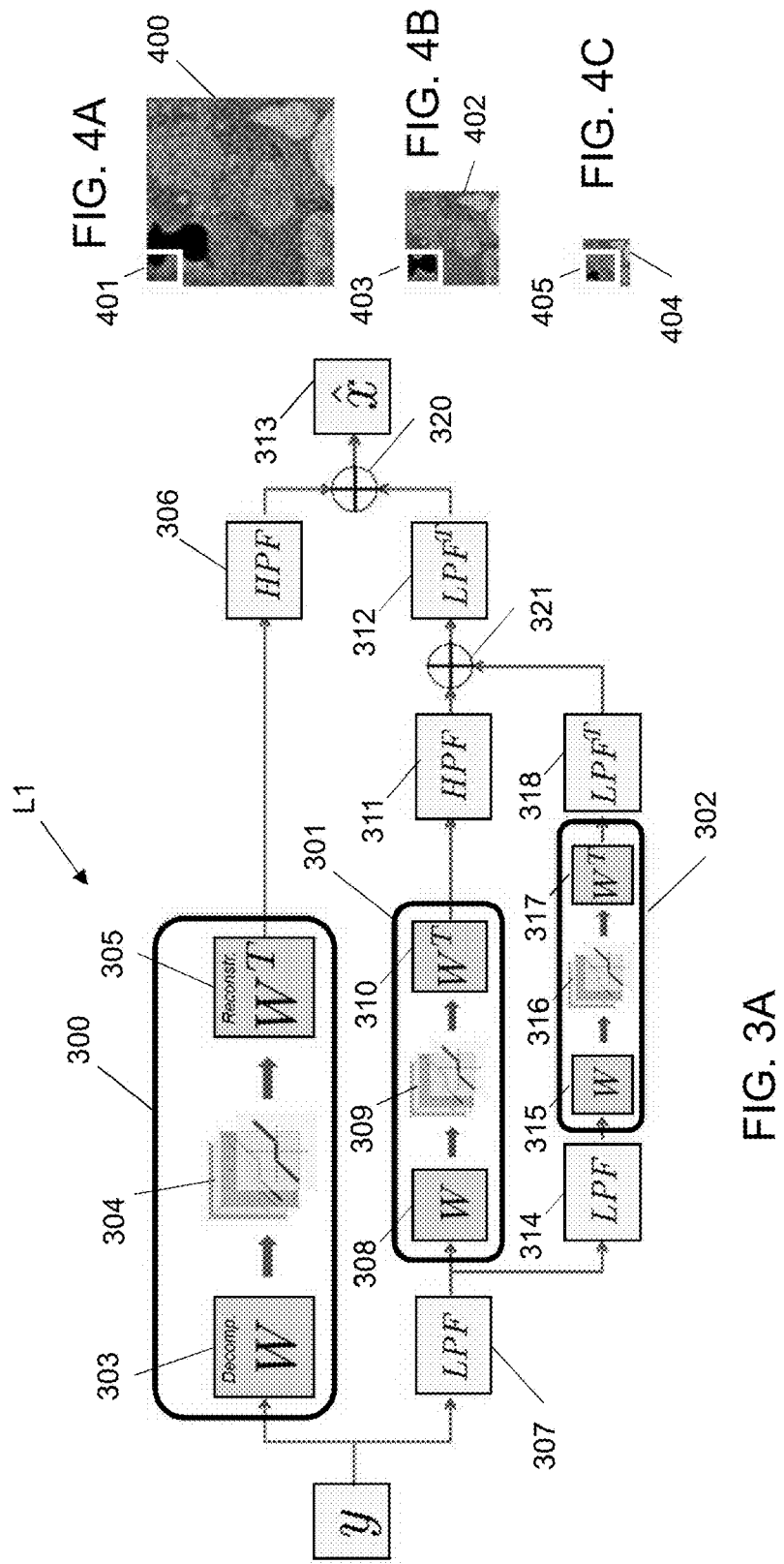
FIG. 3A is a block diagram of an exemplary embodiment of a layer of the DNN of FIG. 2.
FIG. 3B is a diagram of an exemplary embodiment of a decomposition block of the layer of FIG. 2.

FIG. 3A is a detailed block diagram of an embodiment of one layer $L_1$ of the DNN 200 of FIG. 2. The layer L1 of FIG. 3A is a multi-scale denoising autoencoder. Each layer $L_2, \ldots, L_K$ has a structure similar to the structure of layer $L_1$. To be able to achieve good quality of reconstruction, larger patch sizes (e.g., 5×5, 9×9, and 17×17 patches) can be used in the image representation. However, working with larger patches quickly becomes computationally expensive since the number of atoms in the dictionary D grows as well and the cost to decompose a patch increases with its size. To overcome this difficulty, the apparent image self-similarity observed across multiple scales can produce a multiscale patch-based image representation. This representation is based on the idea of subsampling the image and processing its smaller versions with the same dictionary of small patches. When the thresholded and reconstructed patches are up-sampled back to the original size, this strategy corresponds to processing the initial image with larger (albeit simpler) patches.

In FIG. 3A, y is an input image data, and $\hat{x}$ is updated reconstructed image data at the output of the layer L1. The input data y is provided to a decomposition/thresholding/reconstruction (DTR) block 300. The DTR block 300 has a decomposition block 303, which applies a bank W of convolution filters (filter bank) to the input image data array y. FIG. 3B shows an example of a filter bank W. The filter bank W has a plurality of linear filters $F_{1,1}, F_{1,2}, \ldots F_{N,N}$. For example, in various embodiments, the filter bank W can have 10, 15, 20 or 25 filters. Each filter $F_{1,1}, F_{1,2}, \ldots F_{N,N}$ is an array having a predetermined kernel size (e.g., 5×5 or 7×7). The filter coefficients are unknown prior to training, and are determined during training. The filter bank W applies a different decomposition transform to the input image data y, and transforms the image data into a respectively different set of k-space data. For example, the filters can perform a Fourier transform, and each filter can represent the MR image data sensed by a sensor located at a respectively different location relative to the subject. The output of the filter bank W includes M×N images, each representing a respectively different filter response to the image data.

The thresholding block 304 applies a thresholding function to the k-space data. The thresholding function eliminates frequency components having a magnitude smaller than a threshold value. The thresholding function 304 operates separately on each of the filter response array coefficients output from the decomposition block 303. The output of the thresholding block 304 has the same dimensions as the input to the thresholding block 304.

In some embodiments, the thresholding function is non-linear. In some embodiments, the thresholding function has a non-linear value a, which is recursively computed during the training. Note that the thresholding variable a in equations (3) and (4) below is a different parameter from the gradient step a between layers in equation (2) above.

Figure 5:
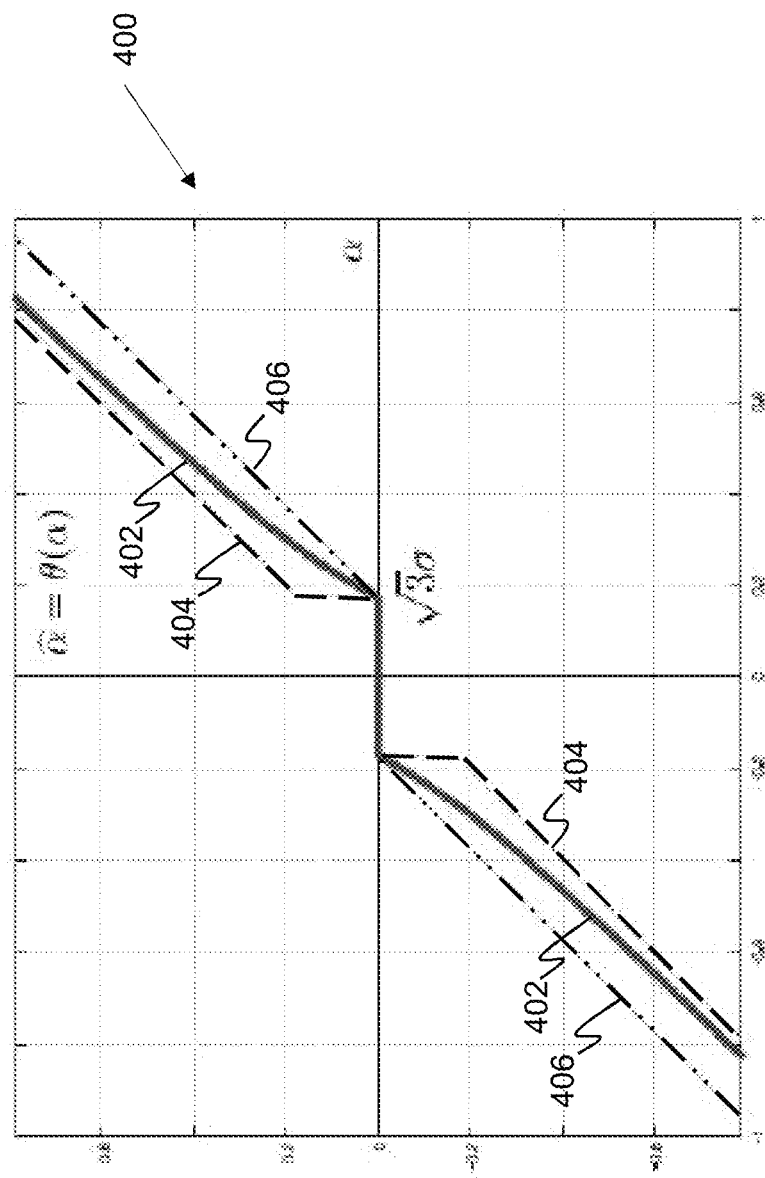
FIG. 5 is a diagram of an exemplary embodiment of a thresholding function for the thresholding block of FIGS. 2 and 3A.

For example, FIG. 5 shows three non-linear thresholding functions 402, 404, and 406. Each of the three thresholding functions has an ordinate value of zero when the value of the abscissa is between $-\sqrt{3}\sigma$ and $\sqrt{3}\sigma$. Thresholding function 406 has the form $y=\alpha-\sqrt{3}\sigma$, if $\alpha>\sqrt{3}\sigma$, and $y=\alpha+-\sqrt{3}\sigma$, if $\alpha<-\sqrt{3}\sigma$. Thresholding function 404 has the form $y=\alpha$, if $\alpha>-\sqrt{3}\sigma$, or $\alpha<-\sqrt{3}\sigma$. In some embodiments, the thresholding function 402 is a garrote function, as shown in FIG. 5 and defined in Equation (3). The thresholding function 402 asymptotically approaches the value of thresholding function 404 for $|\alpha|>>\sqrt{3}\sigma$. That is, the slope of the thresholding function 402 approaches unity for $|\alpha|>>\sqrt{3}\sigma$. In some embodiments, during each iteration of the image reconstruction, a new value $\hat{\alpha}$ and a new value $\sigma$ are computed based on the most recent previous value of $\alpha$, according to the equations:

$$\hat{\alpha} = \frac{(\alpha^2 - 3\sigma^2)_+}{\alpha} \tag{3}$$

and $$\hat{\alpha} = \theta(\alpha) \tag{4}$$

where $\theta$ is the function 402 shown in FIG. 5, a is the parameter learned through training, and the + in the numerator of equation (3) means the positive part, defined as the greater of $\alpha^2-3\sigma^2$ and zero. $\sigma$ is a measure of deviation. $\sigma$ is analogous to a standard deviation of a Gaussian variable, but in this case, the underlying variable is not necessarily Gaussian. With each iteration, $\hat{\alpha}$ and $\sigma$ are refined. By using a thresholding function with a single parameter $\sigma$ to be learned by training, the training is much quicker than is possible with a thresholding function having many parameters.

The thresholding function of FIG. 5 eliminates small coefficients, and asymptotically approaches identity when coefficients are very high, to preserve them. Although the thresholding is mathematically similar to denoising, the components removed are not necessarily noise, and may be aliasing components, for example. The function 404 is identity when far from zero. Function 402 asymptotically approaches the function 404, so the thresholding using the function of function 402 does not lose strong features. The function 406 provides soft thresholding, which can be used for N1 minimization.

Referring again to FIG. 3A, a multiscale patch-based processing system L1, according to some embodiments is shown. This system L1 combines the advantages of patch-based representations with the computational efficiency of multiscale transforms. Briefly, the system L1 decomposes an image and recursively applies a dictionary-based process. The system L1 operates on p×q patches, repeating on further decomposition levels. On each level of decomposition, the subsampled image is processed by a respective block 300, 301, or 302 with patches of the same small size (e.g., 5×5 pixels), which effectively results in using larger patches in the original image (as shown schematically in FIGS. 4A-4C). In FIG. 3A, the number of levels can be set to provide a tradeoff between computational complexity and image quality. Additionally, the number of levels can be capped to avoid over processing the data in a manner that reduces its overall quality. After reconstruction, a high-pass filter (HPF) 306 is applied to recombine the results.

To facilitate decomposition and recursion in the system L1, a low-pass filter (LPF) 307 and a down-sampling operator (not shown) are applied to the input image data y. The down-sampled image data is then used as input into the block 301 and to another LPF 314 and second down-sampling operator (not shown). The once-down-sampled data from LPF 307 are supplied to processing block 301. The twice-down-sampled data from LPF 314 are supplied to processing block 302. As processed twice-down-sampled data from block 302 is returned, an up-sampling operator (not shown) and low-pass filter 318 are applied before combining with the results of the high-pass filter 311. As processed down-sampled data from block 301 is returned, the data are passed through an HPF 311, and combined with the data from LPF 318. an up-sampling operator (not shown) and low-pass filter 312 are applied before combining with the results of the high-pass filter 306 to yield the updated image $\hat{x}$.

To efficiently combine the images reconstructed from patches of different sizes, the patch based processing scheme is combined into a multiscale subsampled representation (such as with an orthogonal wavelet transform) which otherwise achieves perfect reconstruction. Effectively, this places more emphasis on reconstructing higher frequency components (such as sharp edges and fine patterns) with patches of smaller sizes, while low pass filtering in the down-sampled branch suppresses aliasing effects. While the structure presented in FIG. 3A corresponds to three scales of the thresholding algorithm in the layer L1, multiple layers of the network can be stacked sequentially to form a deeper network as shown in FIG. 2. After proper initialization (e.g., using a K-SVD dictionary trained on 5×5 patches to initialize the layers D and R and Daubechies wavelets of 4-pixel support for the corresponding low- and high-pass filters), the entire network can be trained with the backpropagation algorithm on the set of training images. This use of multiple layers in a sequential manner has the effect of increasing both the Peak Signal to Noise Ratio (PSNR) and the structural similarity (SSIM) of the data.

The system 200 in FIG. 2 can be trained such that each layer $L_1, L_2, \ldots, L_K$ learns to reduce the errors/artifacts of the previous layers. The results of the first layer $\hat{x}_1$ are linearly recombined with the original image y. This combination is then used as an input for the next layer L2 in the sequence. After a desired number K of layers (i.e., iterations) the reconstructed image $\hat{x}_K$ is output. In some embodiments, functionality can be included in the system 200 to check for convergence between different levels as the processing is recursively performed.

Referring again to FIG. 3A, the reconstruction block 305 has a bank of filters $W^T$, where $W^T$ is the Hermitian adjoint of W. The reconstruction block 305 applies a respective filter to each of the thresholded k-space data arrays output from the thresholding block 304. The filtered images from all of the filters in reconstruction block 305 are summed together to provide reconstructed image data. The image data output from the DTR block 300 are passed through a high pass filter (HPF) 306, and the higher frequency components are provided to summing node 320.

The DTR blocks 301 and 302 are similar to DTR block 300 in function. DTR block 301 has a decomposition block 308, a thresholding block 309 and a reconstruction block 310, similar to the corresponding blocks 303-305 described above. The filters within the decomposition block 308 and reconstruction block 310 can be the same as, or different from, the coefficients of the filters in DTR block 300. DTR block 302 has a decomposition block 315, a thresholding block 316 and a reconstruction block 317, similar to the corresponding blocks 303-305 described above. The filters within the decomposition block 315 and reconstruction block 317 can be the same as, or different from, the coefficients of the filters in DTR block 300.

The input image data y is passed through a low pass filter (LPF) 307 and then the low frequency components are input to DTR block 301 and LPF 314. The reconstructed images output from DTR block 301 are passed through an HPF 301 and provided to summing node 321. The low frequency components output by low pass filter (LPF) 307 are also input to LPF 314, which can have a lower cutoff frequency than LPF 307. LPF 314 provides the twice low-pass-filtered image data to DTR block 302. The reconstructed image data output from DTR block 302 is passed through LPF 318, and provided to summing node 321. Summing node 321 combines the high frequency components from DTR block 301 and the low frequency components from DTR block 302. The output of summing node 321 is passed through LPF 312. Summing node 320 combines the high frequency components from DTR block 300 and the low frequency components from summing node 321. The low frequency components output from LPF 312 are added to the high frequency components from HPF 306 in the summing node 320 and output as the updated reconstructed image data $\hat{x}$ 313.

Figure 4:
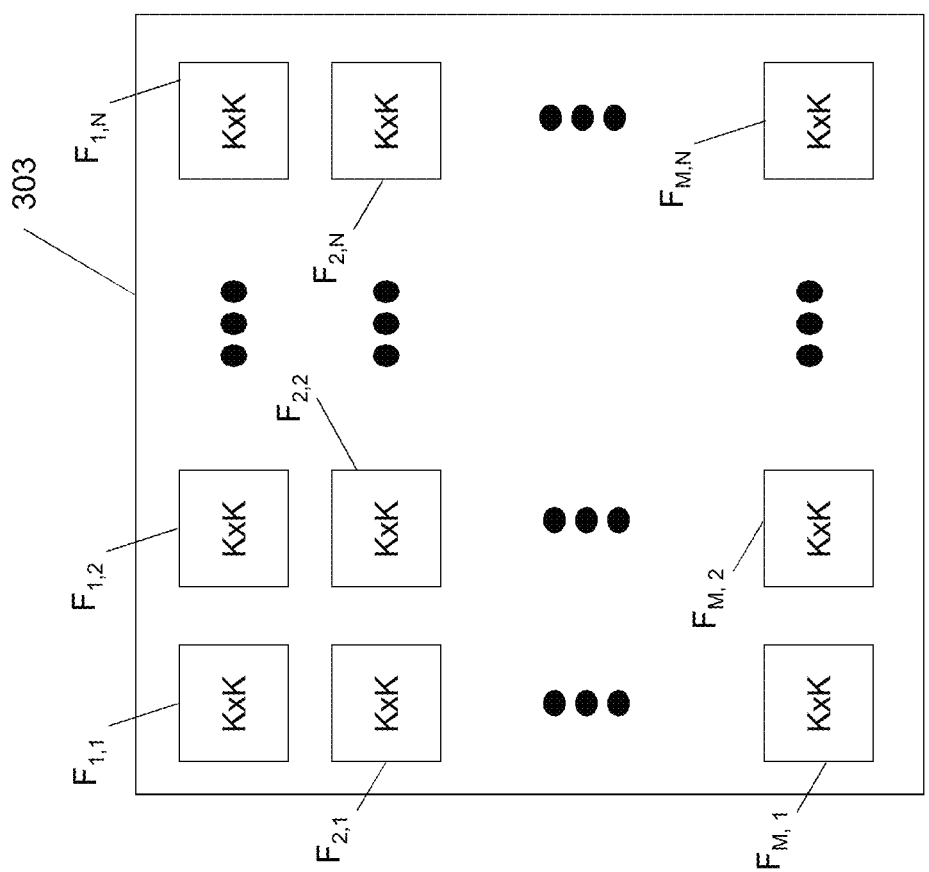
FIGS. 4A, 4B, and 4C schematically show the input image at each of the three scales in FIG. 3A.

FIGS. 4A-4C schematically show an example of an input image 400, 402, and 404 to the filter banks 303, 308 and 315 at all three scales, with the constant size of the W filters represented by the white squares 401, 403, and 405, respectively. The embodiment of FIG. 3A reduces the scale of the image, applies a small filter to the image (which has effectively been zoomed out). Because the image in FIG. 4B is smaller than that of FIG. 4A, the same-sized filter covers a bigger part of the image after down-sizing. Similarly, the filter covers an even larger part of the twice-down-sampled image in FIG. 4C. Thus, using a small filter and a down-sampled image one can obtain results similar to using a large filter on a fully sampled image. This enables the system of FIG. 3A to run faster. To change the size of the image data, a LPF 307, 314 is used, followed by down-sampling.

Referring again to FIG. 2, each of the other layers $L_2, \ldots, L_K$ can be embodied by a multi-scale system as shown in FIG. 3A. As noted above, for training purposes, five to six layers provides good results.

Figure 6:
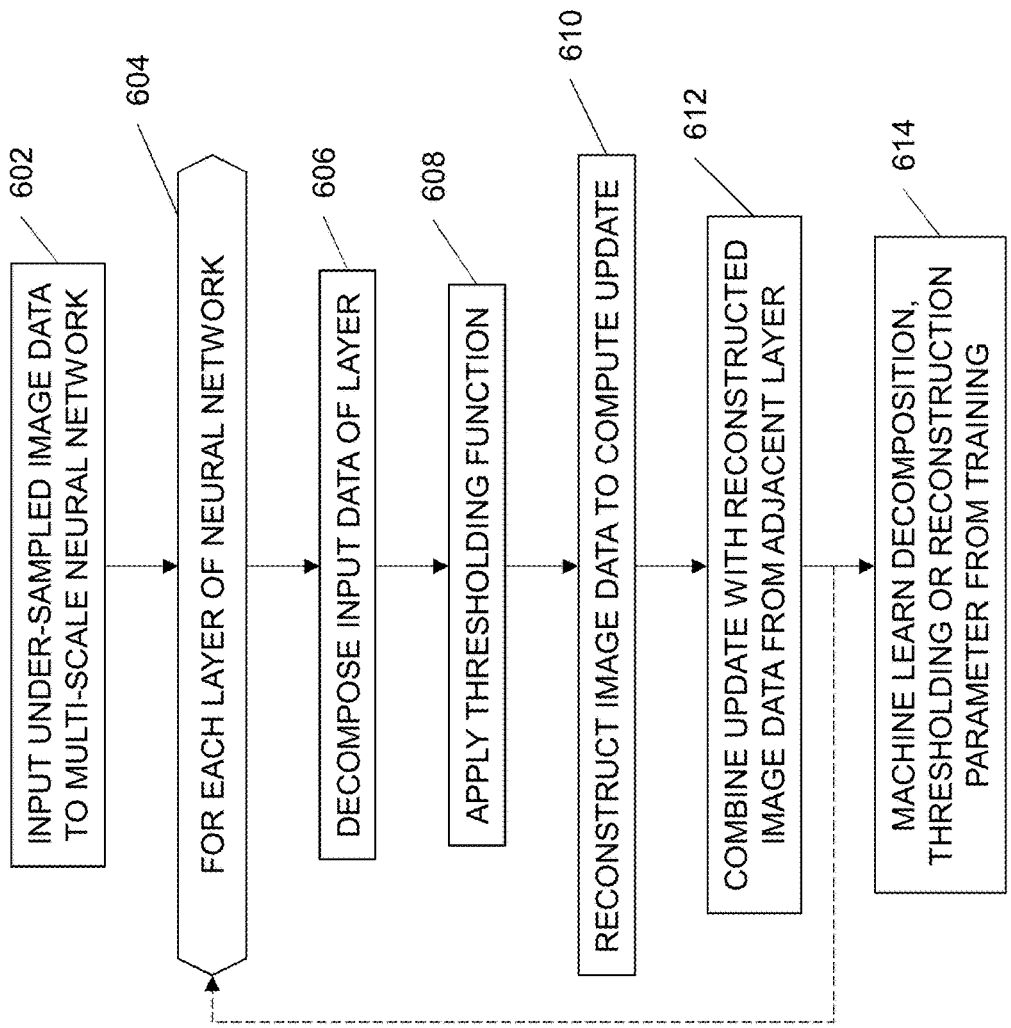
FIG. 6 is a flow chart of a method of obtaining MR image reconstruction parameters by training the system of FIG. 2.

FIG. 6 is a flow chart of an exemplary method for training an MR system to learn the decomposition filter coefficients, thresholding function parameters, and reconstruction filter coefficients.

At step 602, a set of under-sampled image data are input to the multi-scale neural network. The data are under-sampled from a plurality of known fully sampled images. A variety of under-sampling masks can be used. For example, the under-sampling can be performed using a random sampling mask or with a mask optimized to reduce sample coherence.

At step 604, a loop containing steps 606-612 is performed once for each iteration (layer of the DNN).

At step 606, the image data are decomposed into a plurality of filter response arrays of k-space data, corresponding to the convolution of the image data with each respective filter of the filter bank. This transforms the image data to a plurality of k-space data arrays.

At step 608, the k-space data from the decomposition filters are sparsified by applying a thresholding function to each of the k-space data individually, to remove low-magnitude high-frequency components.

At step 610, the thresholded k-space data are reconstructed by deconvolution of the k-space data with a plurality of filters and summing the results of all of the filters. The output of the reconstructed data corresponds to the l1 norm update, $T^H$shrink $(Tx_t)$ from equation (2).

At step 612, the reconstructed image from the previous level of the DNN is added to the l1 norm update computed of step 610 and a regularization update to compute the output of current level of the DNN.

At step 614, after the training image set has been reconstructed, the decomposition, thresholding and/or reconstruction parameters are machine-learned from the trained system.

Figure 7A:
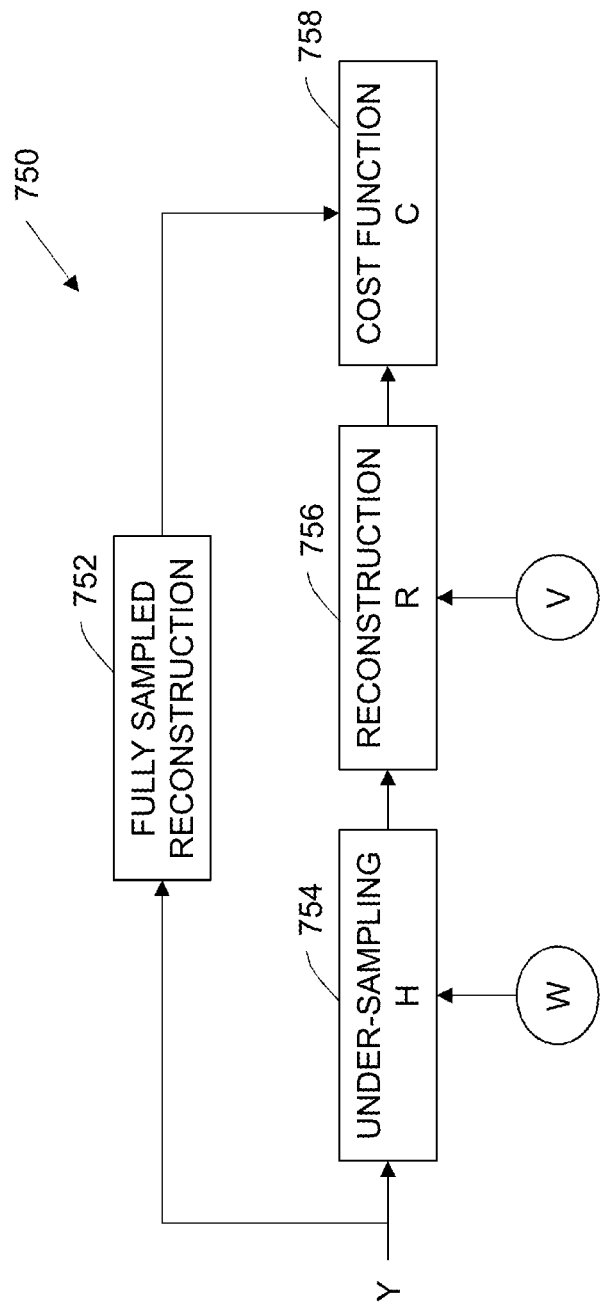
FIG. 7A is a block diagram of an exemplary system for obtaining MR sampling and image reconstruction parameters by training the system of FIG. 2.

FIG. 7A is a block diagram of an exemplary embodiment of a system 750 for machine learning the sampling and reconstruction parameters from training the DNN. As discussed above, the system of FIG. 2 uses machine learning to determine optimized decomposition, thresholding, and reconstruction parameters for use with a particular predetermined sampling mask; to use a different sampling mask, the system of FIG. 2 is re-trained and a new set of decomposition, thresholding, and reconstruction parameters are learned. The embodiment of FIG. 7A does not have a predetermined sampling mask; an optimized sampling operator is machine-learned during training.

In FIG. 7A, the reconstruction block R can be the same as the neural network 200 of FIG. 2, and a description thereof is not repeated. At the input on the left is the "ground truth", i.e., a fully-sampled image, Y. The system of FIG. 7A is configured for learning parameters to reconstruct the image and also learning parameters for under-sampling the image. The whole pipeline (including the under-sampling operator H 754, the reconstruction operator R 756, and the cost function C 758 applies under-sampling and reconstructs images, and then computes the cost function 758 for performing the training. In FIG. 7A, W represents parameters for the image data to be sampled, and V represents parameters for the under-sampling. As the system 750 is trained, it identifies an optimized sampling operator. At the conclusion of the training, the system 750 identifies the under-sampling mask that provides an image data sample optimized to produce the best cost function result.

In some embodiments, the sampling mask is a probability mask. Every measurement has a respective probability of being sampled, the different measurements are sampled or skipped independently from each other, and the probability can be any real number between zero and one. The average loss is an average computed over all masks generated according to the probability distributions during the training. One of the tasks of the training is to learn these probabilities (of each measurement being sampled), i.e. to learn how to acquire the data. In other embodiments (not shown), the mask is a binary mask, and each measurement is either sampled or not sampled.

In FIG. 7A, the parameters V (for reconstruction) include all trainable parameters discussed above for reconstruction (including step size α, threshold σ, decomposition operator D, reconstruction operator R) that are trainable for reconstruction. The parameter H is one particular binary mask, and w is the array containing the probabilities of sampling each individual measurement. Every measurement can have a different probability potential w.

The loss function L(w,v) for is defined by equation (5):

$$L(w, v) = E_{y,H}(C(R(v, H(y)))) \quad (5)$$
$$= \sum_H p(H, w) E_y(C(R(v, H(y))))$$
$$= \sum_H p(H, w) f(H, v)$$

where H(y) is the mask (under-sampling) function, R(v,H) is the reconstruction operator with parameters v and H, C is the cost function, and $E_{y,H}$ is the expected value or average, taken over the image data Y. The under-sampling mask operator H, p(H,w) is the probability of a mask given a specific measurement. $f(H, v)$ is a function of H and v combining the expected value (average) $E_y(C(R(v,H(y))))$ for a given input sample y and reconstruction parameters v.

The under-sampling layer is stochastic both at training and test time. The dependency in the weights w shows up in the total mask probability of H. The loss is averaged over H too. There are a combinatorial number of possible patterns.

The training loss is thus computed by averaging across training data and different masks that can be computed by these probabilities, and then averaging over the masks. Taking the average over the masks means computing the sum of all possible masks of the probability to generate that particular mask, given the probability w of the individual measurements. The sum represents the loss of the data, and does not depend on the individual probabilities anymore. The function $f$ depends only on the under-sampling operator and the parameters of reconstruction.

To model the probability p(H, w), an independent Bernoulli mask model can be used, according to equations:

$$p(H, w) = \prod_i p_i(h_i, w_i) \quad (6)$$

$$p_i(h_i, w_i) = w_i, h_i = 1 \quad (7)$$

This method relaxes the under-sampling problem so the dependence in the weight appears in the probabilities $h_i$ to get the individual mask. The sampling process is modelled as having a probability to pick every measurement, so the probability of the mask as a whole is the product of the probabilities to pick every measurement sampled in that mask.

Given a matrix of probabilities to make masks, a function is used to generate random inputs and apply that to the probability function. The probability to generate the mask H is the product of the probabilities $w_i$ to pick $h_i$ every measurement. For a particular binary mask, there are some measurements that are picked, but have a probability less than one, and some measurements that are not picked have a probability greater than zero. So the probability to get a particular mask is $p_i(h_i, w_i) = w_i$ if that mask $h_i$ is one, and it's $p_i(h_i, w_i) = 1 - w_i$ if that mask $h_i$ is zero. That is, the method selects at random for every voxel whether that measurement is sampled or not, with probability $w_i$. One can compute an estimate of the gradient $$\frac{\partial L}{\partial w_i}(w, v)$$

of the loss using equation (8).

$$\frac{\partial L}{\partial w_i}(w, v) = \sum_H \frac{\partial p}{\partial w_i}(H, w) f(H, v) \qquad (8)$$

$$= \sum_H \prod_{j \neq i} p_j(h_j, w_j) \frac{\partial p_i}{\partial w_i}(h_i, w_i) f(H, v)$$

$$= \sum_H p(H, w) \frac{1}{p_i(h_i, w_i)} \frac{\partial p_i}{\partial w_i}(h_i, w_i) f(H, v)$$

$$= E_H\left(\frac{\partial \log p_i}{\partial w_i}(h_i, w_i) f(H, v)\right)$$

Once the gradient $$\frac{\partial L}{\partial w_i}(w, v)$$

is computed, it can be used when training. When training, process is to take data to generate the mask at random, using the probabilities that are currently computed and to do a gradient step on the weight $$\frac{\partial L}{\partial w_i}(w, v)$$

to try to optimize the probability.

The process of training includes:
using the probability $w_i$ to generate a mask;
then using that mask and data, compute the loss; and
computing the gradient step $$\frac{\partial L}{\partial w_i}(w, v)$$

using that loss, to obtain the probability w. The gradient step $$\frac{\partial L}{\partial w_i}(w, v)$$

is subtracted from w.

The machine learning for the under-sampling operator is performed in a manner similar to that used in the reconstruction steps, but optimizing the mask parameters w, not the image reconstruction parameters v. For the system of FIG. 7A, when training, instead of optimizing over X, or the image data, the machine learning is used to optimize over weights, as described by equation (9):

$$w_{t+1} = w_t - \alpha \frac{\partial L}{\partial w_i}(w, v) \qquad (9)$$

In some embodiments, an extra constraint is added by putting a constraint on the expected total number of samples to have 1 (i.e., the measurement is kept) in the mask for under-sampling the image. Some embodiments add a penalization by summing $w_i$ with a weight $\lambda$. When the penalization is included, there is an extra weight, an extra $\lambda$, in the gradient.

$$w_{t+1} = w_t - \alpha \frac{\partial L}{\partial w_i}(w, v) - \lambda \qquad (10)$$

where $\lambda$=penalization.

Using the above method, the sampling mask and the reconstruction parameters are trained together. In general, the reconstruction will be adapted to the type of under-sampling being used.

Figure 7B:
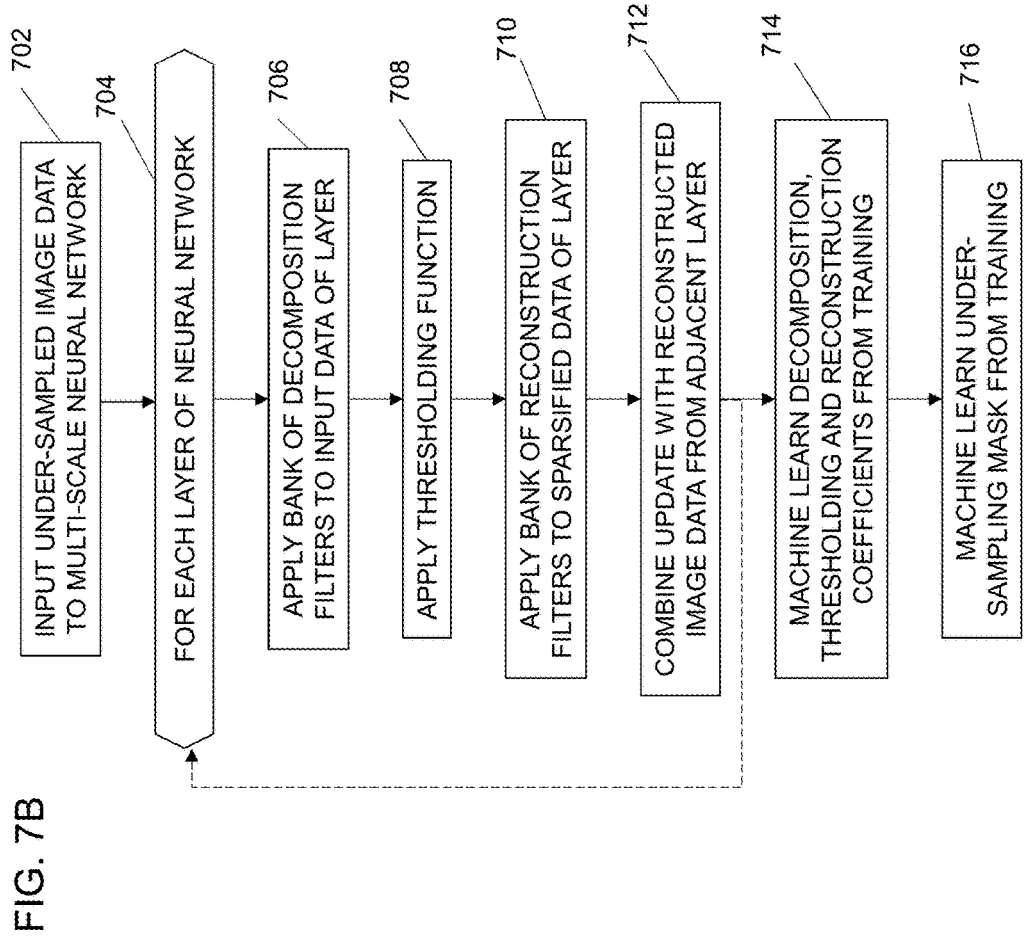
FIG. 7B is a flow chart of a method of obtaining MR sampling and image reconstruction parameters by training the system of FIG. 7A.

FIG. 7B is a flow diagram of a method for learning reconstruction and under-sampling parameters during training of a DNN for reconstructing MR images.

At step 702, a set of under-sampled image data are input to the multi-scale neural network. The data are under-sampled from a plurality of known fully sampled images. A variety of under-sampling masks can be used. For example, the under-sampling can be performed using a random sampling mask or with a mask optimized to reduce sample coherence.

At step 704, a loop containing steps 706-712 is performed once for each iteration (layer of the DNN).

At step 706, the image data are decomposed into a plurality of filter response arrays of k-space data, corresponding to the convolution of the image data with each respective filter of the filter bank. This transforms the image data to a plurality of k-space data arrays.

At step 708, the k-space data from the decomposition filters are sparsified by applying a thresholding function to each of the k-space data individually, to remove low-magnitude high-frequency components.

At step 710, the thresholded k-space data are reconstructed by deconvolution of the k-space data with a plurality of filters and summing the results of all of the filters. The output of the reconstructed data corresponds to the l1 norm update, $T^H$shrink $(Tx_t)$.

At step 712, the reconstructed image from the previous level of the DNN is added to the l1 norm update computed of step 710 and the regularization component to compute the output of the current level of the DNN.

At step 714, after the training image set has been reconstructed, the decomposition, thresholding and/or reconstruction parameters are machine-learned from the trained system.

At step 716 the sampling mask (operator) is machine-learned from the trained system.

FIG. 8A-8H show the performance of the DNN learning results, in mean squared error (MSE) numbers, comparing to traditional iterative algorithms such as Conjugate gradient (CG) sense, and Total Variation (TV) constrained compressed sensing (CS) sense. The CG sense and TV constrained CS sense methods do not use machine learning. The CG sense method is a linear reconstruction, un-regularized without the l1 term.

FIGS. 8A-8H show test data set results, with MSE number labelled. FIG. 8A shows a fully-sampled test image, with an MSE of approximately zero. FIG. 8B shows the result of directly reconstructing under-sampled image data with zero-padding (inserting zeroes for measurements that are not sampled), with an MSE of 4.57. FIG. 8C shows the result of applying the multi-scale model without training (e.g., using random coefficient values in the D and R filters), with an MSE of 17.3. FIG. 8D shows the results using the same multi-scale model after training, providing an MSE of 2.52. FIGS. 8E and 8F show the results of using a CG model after 5 and 20 iterations, yielding MSEs of 4.53 and 4.28, respectively. FIGS. 8G and 8H show the results of suing a TV model after 5 and 20 iterations, yielding MSEs of 3.51 and 2.92, respectively. The learning result (After-training) in FIG. 8D has the best MSE among all of the under-sampled methods (i.e., better than all except for the fully-sampled image of FIG. 8A).

Figure 9:
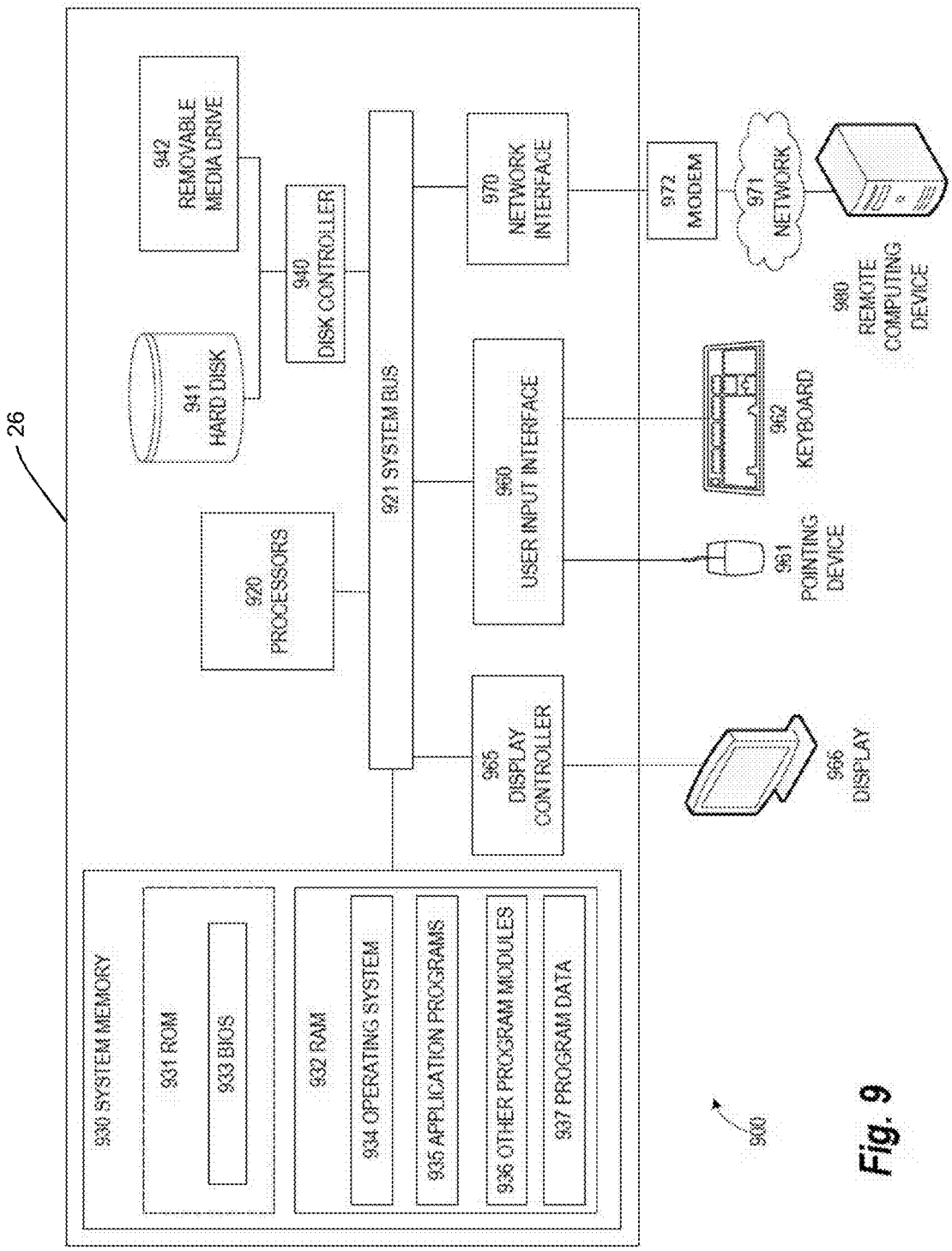
FIG. 9 is a detailed block diagram of an example of the computer system suitable for the system of FIG. 1, according to some embodiments.

FIG. 9 illustrates an exemplary computing environment 900 within which includes an embodiments of the central control system 26 of FIG. 1. For example, computing environment 900 can be used to implement one or more of the deep multi-scale networks described herein. Computers and computing environments, such as central control system 26 and computing environment 900, are known to those of skill in the art and thus are described briefly here.

As shown in FIG. 9, the central control system 26 can include a communication mechanism such as a system bus 921 or other communication mechanism for communicating information within the central control system 26. The central control system 26 further includes one or more processors 920 coupled with the system bus 921 for processing the information.

The processors 920 can include one or more central processing units (CPUs), graphical processing units (GPUs), or any other processor known in the art. More generally, a processor can include a device for executing machine-readable instructions stored on a computer readable medium, for performing tasks and can comprise any one or combination of, hardware and firmware. A processor can also comprise memory storing machine-readable instructions executable for performing tasks. A processor acts upon information by manipulating, analyzing, modifying, converting or transmitting information for use by an executable procedure or an information device, and/or by routing the information to an output device. A processor can use or comprise the capabilities of a computer, controller or microprocessor, for example, and be conditioned using executable instructions to perform special purpose functions not performed by a general purpose computer. A processor can be coupled (electrically and/or as comprising executable components) with any other processor enabling interaction and/or communication there-between. A user interface processor or generator can include electronic circuitry or software or a combination of both for generating display images or portions thereof. A user interface can comprise one or more display images enabling user interaction with a processor or other device.

Continuing with reference to FIG. 9, the central control system 26 also includes a system memory 930 coupled to the system bus 921 for storing information and instructions to be executed by processors 920. The system memory 930 can include computer readable storage media in the form of volatile and/or nonvolatile memory, such as read only memory (ROM) 931 and/or random access memory (RAM) 932. The RAM 932 can include other dynamic storage device(s) (e.g., dynamic RAM, static RAM, and synchronous DRAM). The ROM 931 can include other static storage device(s) (e.g., programmable ROM, erasable PROM, and electrically erasable PROM). In addition, the system memory 930 can be used for storing temporary variables or other intermediate information during the execution of instructions by the processors 920. A basic input/output system 933 (BIOS) containing the basic routines that help to transfer information between elements within central control system 26, such as during start-up, can be stored in the ROM 931. RAM 932 can contain data and/or program modules that are immediately accessible to and/or presently being operated on by the processors 920. System memory 930 can additionally include, for example, operating system 934, application programs 935, other program modules 936 and program data 937.

The central control system 26 can also include a disk controller 940 coupled to the system bus 921 to control one or more storage devices for storing information and instructions, such as a magnetic hard disk 941 and a removable media drive 942 (e.g., floppy disk drive, compact disc drive, tape drive, and/or solid state drive). Storage devices can be added to the central control system 26 using an appropriate device interface (e.g., a small computer system interface (SCSI), integrated device electronics (IDE), Universal Serial Bus (USB), or FireWire).

The central control system 26 can also include a display controller 965 coupled to the system bus 921 to control a display or monitor 966, such as a liquid crystal display (LCD), for displaying information to a computer user. The computer system includes an input interface 960 and one or more input devices, such as a keyboard 962 and a pointing device 961, for interacting with a computer user and providing information to the processors 920. The pointing device 961, for example, can be a mouse, a light pen, a trackball, or a joy stick for communicating direction information and command selections to the processors 920 and for controlling cursor movement on the display 966. The display 966 can provide a touch screen interface which allows input to supplement or replace the communication of direction information and command selections by the pointing device 961.

The central control system 26 can perform a portion or all of the processing steps of embodiments in response to the processors 920 executing one or more sequences of one or more instructions contained in a memory, such as the system memory 930. Such instructions can be read into the system memory 930 from another computer readable medium, such as a magnetic hard disk 941 or a removable media drive 942. The magnetic hard disk 941 can contain one or more data stores and data files used by various embodiments. Data store contents and data files can be encrypted to improve security. The processors 920 can also be employed in a multi-processing arrangement to execute the one or more sequences of instructions contained in system memory 930. In alternative embodiments, hard-wired circuitry can be used in place of or in combination with software instructions. Thus, embodiments are not limited to any specific combination of hardware circuitry and software.

Some embodiments include software instructions written in a high level language, such as C, C++, C#, Java, Fortran or Python. Some embodiments are written for a multi-paradigm numerical computing environment, such as Matlab, sold by Mathworks, Inc. of Natick, Mass., or the like.

As stated above, the central control system 26 can include at least one computer readable medium or memory for holding instructions and for containing data structures, tables, records, or other data described herein. The term "computer readable medium" as used herein refers to any non-transitory machine-readable storage medium that participates in providing instructions to the processors 920 for execution. A computer readable medium can take many forms including, but not limited to, non-transitory, non-volatile media and volatile media. Non-limiting examples of non-volatile media include optical disks, solid state drives, magnetic disks, and magneto-optical disks, such as magnetic hard disk 941 or removable media drive 942. Non-limiting examples of volatile media include dynamic memory, such as dynamic random access memory 930.

The central control system 26 can operate in a networked environment using logical connections to one or more remote computers, such as remote computing device 980. Remote computing device 980 can be a personal computer (laptop or desktop), a mobile device, a server, a router, a network PC, a peer device or other common network node, and typically includes many or all of the elements described above relative to central control system 26. When used in a networking environment, central control system 26 can include modem 972 for establishing communications over a network 971, such as the Internet. Modem 972 can be connected to system bus 921 via user network interface 970, or via another appropriate mechanism.

Network 971 can include, but is not limited to, the Internet, an intranet, a local area network (LAN), a wide area network (WAN), a metropolitan area network (MAN), a personal area network (PAN) a direct connection or series of connections, a cellular telephone network, or any other network or medium capable of facilitating communication between central control system 26 and other computers (e.g., remote computing device 980). The network 971 can be wired, wireless or a combination thereof. Wired connections can be implemented using Ethernet, Universal Serial Bus (USB), RJ-6, or any other wired connection. Wireless connections can be implemented using Wi-Fi, WiMAX, and Bluetooth, infrared, cellular networks, satellite or any other wireless connection methodology. Additionally, several networks can work alone or in communication with each other to facilitate communication in the network 971.

Aside from the computing environment 900 shown in FIG. 9, the methods and systems described herein can be implemented in specialized computing environments. For example, in some embodiments, a plurality of processors can be configured to parallelize at least one of the decomposition operations, the non-linear thresholding, and/or the reconstruction operations performed by the neural networks described above. These processors can be arranged, for example, in a parallel computing platform using technologies such as "Apache Spark™" or "NVIDIA CUDA™".

The functions and process steps described herein can be performed automatically or wholly or partially in response to user command. An activity (including a step) performed automatically is performed in response to one or more executable instructions or device operation without user direct initiation of the activity.

The methods and system described herein can be at least partially embodied in the form of computer-implemented processes and apparatus for practicing those processes. The disclosed methods can also be at least partially embodied in the form of tangible, non-transitory machine readable storage media encoded with computer program code. The media can include, for example, RAMs, ROMs, CD-ROMs, DVD-ROMs, BD-ROMs, hard disk drives, flash memories, or any other non-transitory machine-readable storage medium, wherein, when the computer program code is loaded into and executed by a computer, the computer becomes an apparatus for practicing the method. The methods can also be at least partially embodied in the form of a computer into which computer program code is loaded and/or executed, such that, the computer becomes a special purpose computer for practicing the methods. When implemented on a general-purpose processor, the computer program code segments configure the processor to create specific logic circuits. The methods can alternatively be at least partially embodied in a digital signal processor formed of application specific integrated circuits for performing the methods.

Although the subject matter has been described in terms of exemplary embodiments, it is not limited thereto. Rather, the appended claims should be construed broadly, to include other variants and embodiments, which can be made by those skilled in the art.

What is claimed is:

1. A method for training a system for reconstructing a magnetic resonance (MR) image from signals collected by an MR scanner, the method comprising:

under-sampling respective image data from each of a plurality of fully-sampled images;

inputting the under-sampled image data to a multi-scale neural network comprising a plurality of sequentially connected layers, each layer having a respective input for receiving a respective array of input image data and an output for outputting reconstructed image data, each layer performing a recursive process comprising:

decomposing the array of input image data received at the input of the layer;

applying a thresholding function to the decomposed image data, to form shrunk data, the thresholding function outputting a non-zero value asymptotically approaching one when the thresholding function receives an input having a magnitude greater than a first value, reconstructing the shrunk data for combining with a reconstructed image data output by another one of the plurality of layers to form updated reconstructed image data, and machine-learning at least one parameter of the decomposing, the thresholding function, or the reconstructing based on the fully sampled images and the updated reconstructed image data.

2. The method of claim 1, wherein the thresholding function outputs a zero value in the case where the thresholding function receives an input having a magnitude less than the first value.

3. The method of claim 2, wherein the thresholding function is non-linear.

4. The method of claim 3, wherein the thresholding function is a garrote function.

5. The method of claim 2, wherein each layer of the multi-scale neural network is configured to update the thresholding function.

6. The method of claim 1, wherein the machine-learning includes machine-learning parameters of the decomposing, the thresholding function, and the reconstructing based on the fully sampled images and the reconstructed image data.

7. The method of claim 1, wherein:
the decomposing includes performing a convolution of the image data and a first filter, and
the reconstructing includes performing deconvolution of the shrunk data and the filter.

8. The method of claim 1, wherein the thresholding function of each of the plurality of layers is a shrinkage function.

9. The method of claim 1, wherein each layer is configured for adding a gradient update to the reconstructed image data, and the gradient update is based on a gradient step size recursively computed based on the image data.

10. The method of claim 1, wherein the under-sampling is performed using an under-sampling operator, and the method for training further comprises machine-learning at least one parameter of the under-sampling operator based on the fully sampled images and the updated reconstructed image data.

11. The method of claim 1, wherein the computing includes generating a sampling mask based on the fully sampled images and the updated reconstructed image data.

12. A system for acquiring and reconstructing a magnetic resonance (MR) image from signals collected by an MR scanner, the system comprising:
a non-transitory machine readable storage medium for storing under-sampled image data from a plurality of fully-sampled images;
a multi-scale neural network for receiving the under-sampled image data, the multi-scale neural network comprising a plurality of sequentially connected layers, each layer having a respective input for receiving a respective array of input image data and outputting reconstructed image data, each layer configured for performing a process comprising:
decomposing the array of input image data received at the input of the layer,
applying a thresholding function to the decomposed image data, to form shrunk data, the thresholding function outputting a non-zero value asymptotically approaching one when the thresholding function receives an input having a magnitude greater than a first value,
reconstructing the shrunk data for combining with a reconstructed image data output by another one of the plurality of layers to form updated reconstructed image data, and
machine-learning at least one parameter of the decomposing, the thresholding function, or the reconstructing based on the fully sampled images and the updated reconstructed image data.

13. The system of claim 12, further comprising:
a pseudo-random generator to generate a sampling mask according to a set of probabilities learned in the multi-scale neural network,
wherein the MR scanner acquires the under-sampled image data from the subject using the sampling mask.

14. The system of claim 12, wherein the thresholding function outputs a zero value in the case where the thresholding function receives an input having a magnitude less than the first value.

15. The system of claim 14, wherein the thresholding function is non-linear.

16. The system of claim 15, wherein the thresholding function is a garrote function.

17. The system of claim 14, wherein each layer of the multi-scale neural network is configured to update the thresholding function.

18. The system of claim 12, wherein the machine-learning includes machine-learning parameters of the decomposing, the thresholding function, and the reconstructing based on the fully sampled images and the reconstructed image data.

19. The system of claim 12, wherein:
the decomposing includes performing a convolution of the image data and a first filter, and
the reconstructing includes performing deconvolution of the shrunk data and the filter.

20. A non-transitory, machine readable storage medium encoded with computer program software, such that when a processor executes the computer program software, the processor performs a method for training a system for reconstructing a magnetic resonance (MR) image from signals collected by an MR scanner, the method comprising:
under-sampling respective image data from each of a plurality of fully-sampled images;
inputting the under-sampled image data to a multi-scale neural network comprising a plurality of sequentially connected layers, each layer having a respective input for receiving a respective array of input image data and an output for outputting reconstructed image data, each layer performing a recursive process comprising:
decomposing the array of input image data received at the input of the layer;
applying a thresholding function to the decomposed image data, to form shrunk data, the thresholding function outputting a non-zero value asymptotically approaching one when the thresholding function receives an input having a magnitude greater than a first value,
reconstructing the shrunk data for combining with a reconstructed image data output by another one of the plurality of layers to form updated reconstructed image data, and
machine-learning at least one parameter of the decomposing, the thresholding function, or the reconstructing based on the fully sampled images and the updated reconstructed image data.

* * * * *